United States Patent [19]

Roy et al.

[11] 4,114,202

[45] Sep. 19, 1978

[54] PROSTHETIC VALVE ASSEMBLY FOR USE IN CARDIOVASCULAR SURGERY

[76] Inventors: Henry A. Roy, 1817 Market St., Warren, Pa. 16365; George J. D'Angelo, R.D. #1, Box 156, Fairview, Pa. 16415

[21] Appl. No.: 763,565

[22] Filed: Jan. 28, 1977

[51] Int. Cl.² .............................................. A61F 1/22
[52] U.S. Cl. ........................................ 3/1.5; 137/512; 137/527; 251/284
[58] Field of Search ................... 137/512, 512.15, 527, 137/527.2, 527.4, 527.6, 527.8; 3/1.5; 251/298, 299, 303, 284; 211/168, 170, 171

[56] References Cited

U.S. PATENT DOCUMENTS

| | | | |
|---|---|---|---|
| 3,370,305 | 2/1968 | Goott et al. | 3/1.5 |
| 3,689,942 | 9/1972 | Rapp | 3/1.5 |
| 3,717,883 | 2/1973 | Mosher | 3/1.5 |
| 3,861,416 | 1/1975 | Wichterle | 137/849 |
| 3,938,197 | 2/1976 | Milo | 3/1.5 |

*Primary Examiner*—William R. Cline
*Attorney, Agent, or Firm*—Munroe H. Hamilton

[57] ABSTRACT

Cardiovascular malfunction is corrected by implantation through open-heart surgery of a prosthetic valve assembly in which a specially formed valve retainer ring, designed to be secured within a blood vessel by means of sutures, supports a plurality of valve flaps in uniquely hinged relationship. The hinged valve flaps are arranged to normally occur in a closed position in which adjacent flap edges, when in abutting relation to one another, limit hinging movement in one direction. The valve flaps are designed to closely resemble valve flaps in a human heart with hinged mountings devised to insure pronounced longevity being provided. Each valve flap, in response to systolic pressure, is free to move away from the normally closed position described. There is thus produced a central passageway through which fluid may flow in a substantial linear path of travel with little, if any, turbulence or traumatic effects being induced. During systole, as well as diastole, flow of fluid between the valve flaps and adjacent inner surfaces of the retainer ring is prevented to avoid formation of blood clots. The shape of the valve flaps may vary and may, for example, be of cuspate form for use in the aorta, or they may be semicircular in form for replacing a mitral valve, or they may be of other shapes.

5 Claims, 21 Drawing Figures

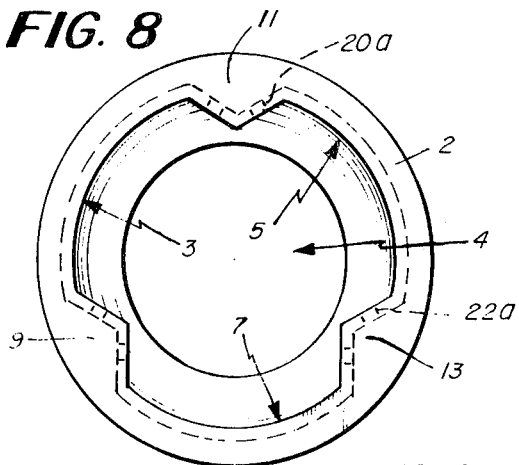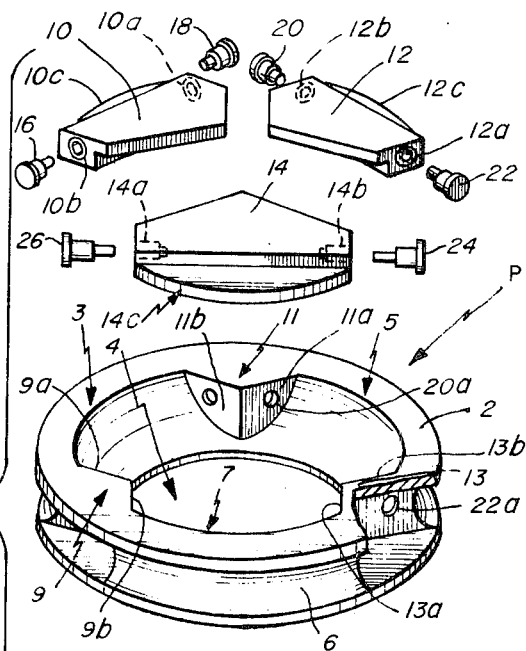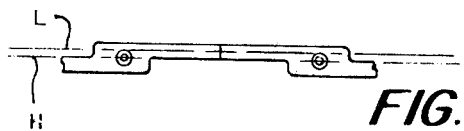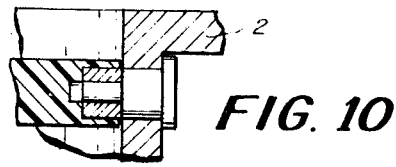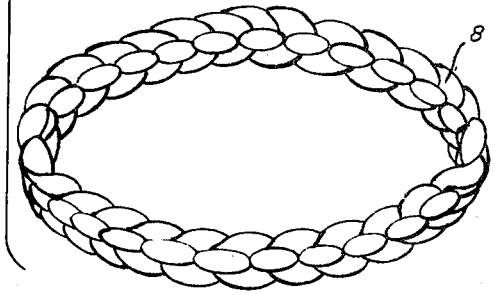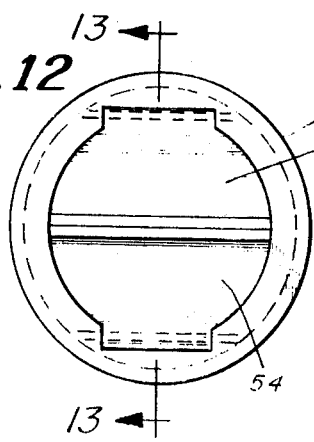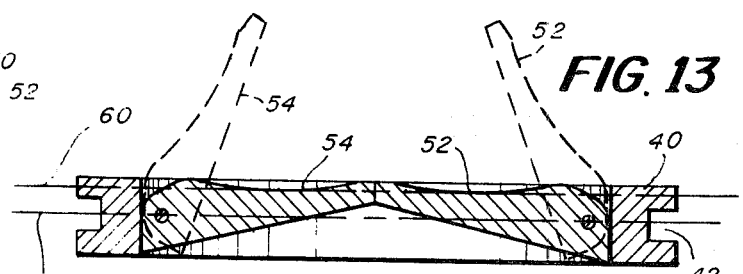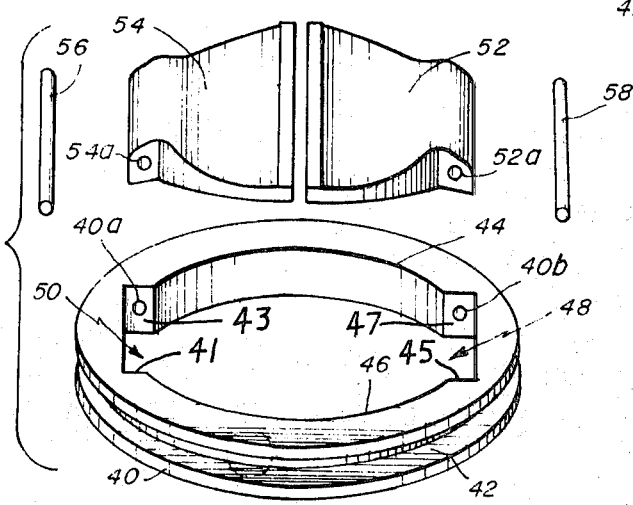

PROSTHETIC VALVE ASSEMBLY FOR USE IN CARDIOVASCULAR SURGERY

BACKGROUND OF THE INVENTION

In the field of open-heart surgery, the use of prosthetic valve devices is well known in the art, and varying forms of such valves are employed for replacement of the aortic valve, the mitral valve, and others.

In thus implanting a prosthetic device in a living body, it is necessary to satisfy several requirements. Thus the valve must, of necessity, be capable of operating continuously for relatively long periods of time without excessive wear or malfunction. Passage of blood through the valve must be carried out in such a way that traumatic effects are avoided and red blood cells are not broken down into white cells. Still further, any condition which may induce the occurrence of blood clotting has to be carefully avoided, and there must be freedom from turbulence or flutter or other condition which would cause patient discomfort.

In one early form of valve structure, a ball valve is used in which a ball member is loosely contained in a supporting cage. It has been found that this device is unsatisfactory in that the ball member, in its cage, presents an objectionably high profile, and the ball, in returning to its seat in the cage, tends to break down red cells to a troublesome degree. Such valves are used very little at the present time.

Another form of valve presently being utilized is a disc valve. With this valve in an open position, flow of blood shoots out in an angular path, tending to create undesirable turbulence, and there is also a tendency for blood to flow behind the valve in an objectionable manner.

Various other valve structures are described in Vol. 154, *American Surgery*, page 726, 1961.

A number of other valve structures are disclosed in recently issued patents including U.S. Pat. Nos. 3,312,237; 3,800,403; 3,861,416; and 3,116,562.

All of the valve structures disclosed in these patents are, so far as we are aware, incapable of satisfying all of the requirements noted above, and there continues to be a need for a more satisfactory valve means of the class indicated.

SUMMARIZATION OF THE INVENTION

The present invention is, in general, concerned with an improved hinged valve construction for controlling flow of fluid through a fluid passageway so that a pulsating flow of fluid moving through the passageway is free from any appreciable turbulence during periodic opening and closing of a plurality of valve elements.

More specifically, the invention is directed to a prosthetic valve construction which is designed to be secured internally of a fluid passageway for replacing valve elements of the heart such as the aortic valve, the mitral valve, or other blood vessel.

It is a chief object of the invention, therefore, to provide an improved valve assembly and to devise especially a valve structure which is capable of functioning steadily as a prosthetic member over relatively long periods of time in the human body.

Another object of the invention is to provide a valve structure of the type indicated having a plurality of valve elements movable into and out of closed positions in response to systolic pressure to permit a smooth flow of fluid free from any appreciable turbulence and to further provide for the movement of the valve elements being limited in one direction.

Still another object of the invention is to provide an arrangement of valve elements through which blood may flow during periodic opening and closing of the valve elements without any traumatic effects being induced in the blood, and without creating conditions which may lead to the formation of blood clots.

Summarizing the invention, it has been determined that the foregoing objectives may be realized to a highly practical degree by means of novel valve assemblies in each of which a plurality of valve flap elements are supported in a special ring body in uniquely hinged relationship. With the hinged mountings disclosed, the valve flap elements are capable of functioning in a manner closely resembling the functioning of valve flaps in the human heart such as the cuspate valve flaps in the aortic valve as well as the mitral valve flaps in the mitral valve.

An important feature of the invention is the construction of a retainer ring body whose inner periphery is recessed to provide hinging apertures within which a plurality of valve flap elements, having specially formed outer hinging extremities, are arranged to mate in hinging relationship.

Each of the hinging apertures is defined by a pair of spaced apart parallel guide surfaces, and the hinging extremities are formed with respective flat sides which are closely confined and guided between the parallel surfaces during rotative movement of the valve flaps into and out of closed positions. Axes of hinging for the valve flaps of constantly maintained precision is thereby realized and this insures extended operating life.

A second major feature of the invention is the mounting of the valve flaps in such a manner that hinging of each flap is contained within a predetermined arc of travel, and movement of the valve flaps is thus limited in one direction as they reach a position of closure in which they abut one another.

The nature of the invention and its other objects and novel features will be more fully understood from the following description of the drawings and disclosure relating thereto.

BRIEF DESCRIPTION OF THE DRAWINGS

FIG. 8 is a plan view of the retainer ring body shown in FIG. 5, but with valve flap elements removed.

FIG. 9 is a fragmentary detail view illustrating portions of a valve flap element in elevation.

FIG. 10 is a cross sectional view taken on the line 10—10 of FIG. 5.

FIG. 11 is an exploded view showing the several valve components in perspective.

FIGS. 12 to 14 are views of a modified form of valve flap and retaining ring assembly wherein a pair of valve flaps of a shape generally resembling the valve flaps of a mitral heart valve are supported on hinging means of the type shown in FIGS. 5 to 11, inclusive.

DETAILED DESCRIPTION OF THE DRAWINGS

The valve structures of the present invention have originated out of a long period of study of existing prosthetic valve devices and utilization of preferred forms of these existing devices in extensive open-heart surgery. From a careful evaluation of performance levels of these existing valve devices, there has been conceived combinations of valve components and hinging means which are believed to be capable of functioning cooperatively with one another to provide significant improvements.

In one desirable form, this combination of valve components is directed toward emulating as closely as possible the structure and functioning of the cuspate valve flaps of the aortic valve in the human heart. A basic concept has been to protectively contain a plurality of prosthetic valve flaps in a ring body in such a manner as to provide restricted hinging movement corresponding to that of human heart valve flaps, and to regulate flow of blood along a controlled path of travel which is substantially free from turbulence. This basic concept has been embodied in three different structural forms including the form of FIGS. 1 to 11, the form of FIGS. 12 to 14, and finally, the form shown in FIGS. 15 to 21.

The principal parts of the valve structure of the invention, exemplified by all of the forms referred to, include a retainer ring body, and a plurality of valve flap elements together with bearing means such as bearing pins for mounting the flap elements inside the ring body in a uniquely hinged relationship. To receive the valve structure inside a fluid passageway such as a blood vessel, there is further provided a suturing collar fitted around the outer peripheral surface of the ring body.

In one desirable form of the invention, the retainer ring body is combined with three cuspate valve flaps particularly constituted to replace the aortic valve flaps of the human heart, and the invention, in this form, is first described with reference being had to FIGS. 1 through 11 of the drawings. Another desirable arrangement for combining a retainer ring body with three cuspate valve flaps is illustrated in FIGS. 15 through 21. However, it should be understood that the invention is not limited to a three-valve flap arrangement, and may be comprised by a pair of semilunar valve flaps, as illustrated in FIGS. 12 to 14, inclusive, or may take other forms.

Figure 1:
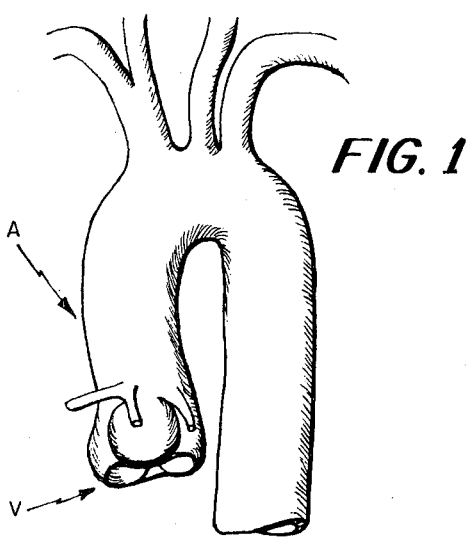
FIG. 1 is a diagrammatic view illustrating schematically the arch of the aorta and its branches, and indicating generally that region where an aortic valve replacement takes place.
Figure 2:
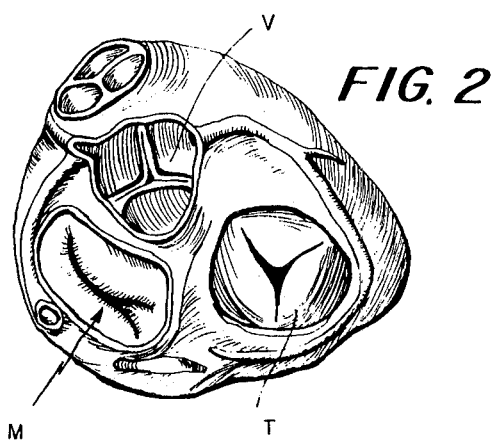
FIG. 2 is another diagrammatic view illustrating a portion of a human heart with the base of ventricles exposed by removal of the atria, and indicating in particular the aortic valve which is replaceable by the prosthetic valve structure of the invention.

Referring to the subject matter illustrated in FIGS. 1 to 11, inclusive, there is indicated diagrammatically in FIG. 1 parts of the aortic arch generally denoted by the arrow A, and within which a flow of blood is conducted after passing through the aortic valve, generally indicated by the arrow V. In FIG. 2, the valve V is further shown in relation to a ventricle portion of a human heart in which is also illustrated a mitral valve M and a tricuspate valve T.

Figure 3:
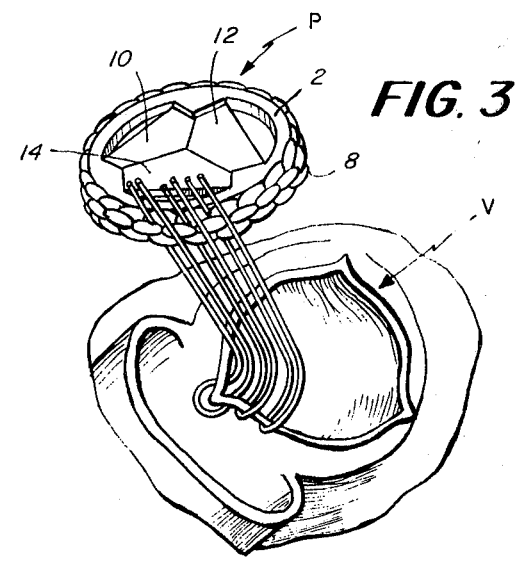
FIG. 3 is another diagrammatic view illustrating the valve structure of the invention in perspective, and indicating a step of suturing being carried out.
Figure 4:
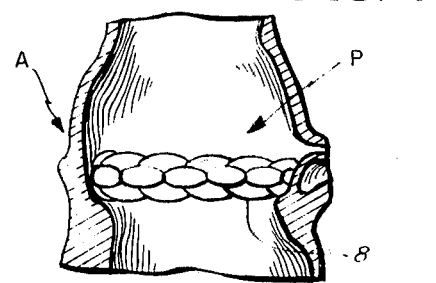
FIG. 4 is a fragmentary detail view of the valve structure of the invention attached in a position to replace an aortic valve.
Figure 6:
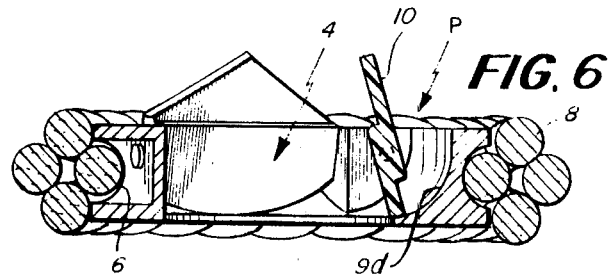
FIG. 6 is a cross section taken on the line 6—6 of FIG. 5.

In FIG. 3, the prosthetic valve of the invention, generally denoted by the arrow P, is shown in perspective in one typical suturing position for attachment to incised portions of the aortic valve V.

Considering in more detail the valve components of the invention designed to replace an aortic valve such as that suggested in FIGS. 1 and 2, numeral 2 (FIG. 8) denotes a retainer ring body which, as shown in FIG. 8 and also FIG. 11, defines a fluid passageway 4. The retainer ring body may be made of metal, plastic, or other suitable materials. As is most clearly shown in FIG. 11, the outer periphery of ring body 2 is formed with a grooved surface 6 in which is secured a suturing collar 8, as suggested in FIGS. 5 and 7.

The suturing collar 8 is designed to be securely fastened around the grooved surface 6, and may be made of a woven plastic material or other substance which is capable of functioning satisfactorily over extended periods of time. One suitable material is a woven product of polyester fibres made from polyethylene terephthalate commonly referred to as DACRON.

In accordance with the invention, the ring body 2 is constructed with specially formed hinging apertures in which a plurality of valve elements are mounted for restricted hinging movement. As is most clearly shown in FIG. 11, there are three of these hinging apertures and they occur in spaced apart relationship to one another and present curved surfaces 3, 5, and 7, separated by inwardly projecting hinge bearing portions 9, 11, and 13.

An important feature of the invention is the combination of the three hinging apertures with the separated bearing portions 9, 11, and 13. The bearing portions in each instance are uniquely constructed with converging hollow side walls which define small V-shaped chambers lying inside of the groove 6, as may be more clearly seen from an inspection of the broken away parts of the projecting bearing portion 13 in FIG. 11.

It is pointed out that the side walls of each bearing portion are further arranged to extend inwardly at predetermined angles such that they occur in parallel relationship to side walls of adjacent bearing portions to thereby constitute sets of spaced apart guide surfaces. Thus the bearing portion 11 presents side walls 11a and 11b. Bearing portion 9 presents side walls 9a and 9b, and bearing portion 13 presents side walls 13a and 13b. The arrangement of these parts is such that the side wall 11a is parallel to side wall 13b and constitutes one set of guide surfaces. The side wall 11b is parallel to the side wall 9a and forms a second set of guide surfaces, and the side wall 13a is parallel to side wall 9b and provides a third set of guide surfaces.

Received in the hinging apertures between the sets of guide surfaces of respective bearing portions are three valve flap elements 10, 12, and 14. Each of the valve flaps, as is most clearly shown in FIG. 11, are of cuspate form and have pointed inner ends designed to meet in abutting relationship to one another. Outer ends of the valve elements are offset and made of increased thickness to comprise hinging extremities. Each extremity is further formed with flat sides which are constructed and arranged to lie between respective sets of guide surfaces in the bearing portions 9, 11 and 13, earlier described. The hinging extremities are mounted for restricted hinging movement on bearing pin means so that the flat sides of the extremities may swing around and be guided by respective sets of guide surfaces.

Figure 5:
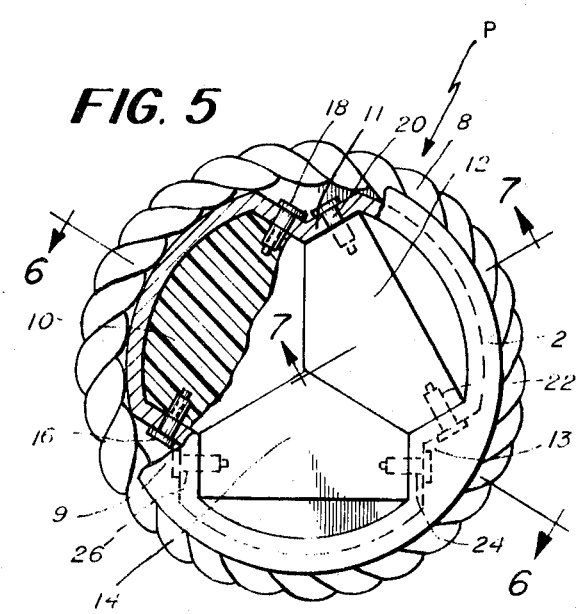
FIG. 5 is a plan view of the valve of the invention.
Figure 7:
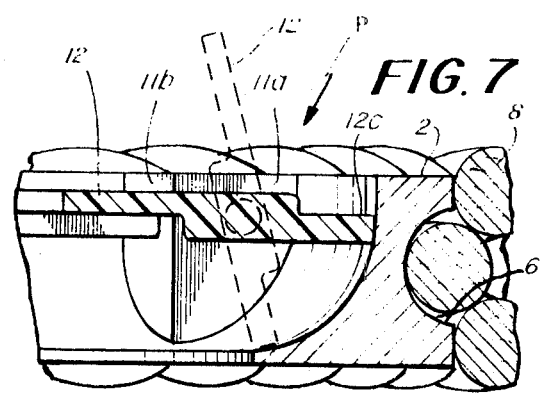
FIG. 7 is a cross section taken on the line 7—7 of FIG. 5.

The bearing pin means in one desirable form may be comprised by sets of bearing pins including one set of bearing pins 16 and 18, as indicated in the broken-away portion of FIG. 5. A second set of pins is denoted by the numerals 20 and 22, and a third set are denoted by numerals 24 and 26. Hinging movement on the pin means described takes place along axes of hinging which extend chordally of the ring body 2.

It will be understood that the valve elements may also be mounted for hinging movement on other forms of bearing means such as, for example, bearing pins extending all the way through respective valve elements, or in other ways.

Each set of bearing pins is received through bearing pin openings as shown in FIG. 11 in which bearing pin 20 is fitted into a pin opening 20a and bearing pin 22 is fitted into a bearing pin opening 22a. Inner reduced extremities of pins 20 and 22 are rotatably mounted in openings 12a and 12b formed in opposite ends of the valve flap element 12. Similarly, ends of pins 16 and 18 are rotatably mounted in openings 10a and 10b in valve flap element 10, and ends of pins 24 and 26 are rotatably mounted in openings 14a and 14b of flap element 14.

It will be noted that the V-shaped spaces defined by the converging hollow wall construction of the bearing portions 9, 11, and 13 provide convenient access ways for installation of the bearing pin elements through the retainer ring 2 into the valve flap openings. It is also pointed out that the suturing collar 8 may be snugly attached around the groove 6 after the pins are installed and may then comprise a covering for closing and substantially sealing off the V-shaped spaces to thereby protectively contain the heads of the hinging pins in a desirable manner.

Another important feature of the invention is the structural form of the valve flap elements themselves, as will be observed in FIG. 11, especially. As earlier noted, each cuspate valve element has a pointed end portion of one thickness and an outer hinging portion of another thickness. With this offset body construction, the pin openings can be located so as to limit hinging movement of the valve flap elements in one direction. It will be apparent that by locating the pin elements in each of the valve elements so that an axis of hinging is established which lies outside the central axis of the relatively thin portions of the flap elements, hinging movement will be restricted. This is more clearly illustrated in FIG. 9 in which is shown an axis of hinging denoted by the line H lying outside of the center line L passing through the thinner flap portion of the valve element. By means of this arrangement, the flaps 10, 12, and 14 are free to move into an open position such as that shown in FIG. 6, but when moved back into a position in which edges of the flap elements abut one another, they can go no further and are effectively restricted to this position of closure.

In addition to the structural valve features above-described, these valve elements may also be designed to lie in close proximity to adjacent surfaces of the hinging apertures in a position to substantially exclude flow of fluid therebetween when the valve elements are opened and closed. This is achieved by forming the offset hinging portions of the valve elements with curved outer edges 10c, 12c, 14c, whose arcs of curvature correspond to respective arcs of curvature of the edges 3, 5 and 7 defining the hinging apertures. The surfaces of the hinging apertures may also have lower concaved parts, as indicated at 9d in FIG. 6, to provide for the valve edges more completely closing the spaces between these edges and the concaved parts when the valve elements are in a fully opened position.

FIGS. 12 to 14, inclusive, there is illustrated another desirable form of the invention in which only two valve flap elements are employed, and this two-valve structure may also be used to replace the aortic valve of a human heart, or may be used for other purposes. Numeral 40 denotes a retainer ring body which defines an inner passageway through which fluid may pass. The outer periphery of the ring body 40 is formed with a groove 42 in which may be received a suturing collar similar to the collar 8, described in reference to the valve of FIGS. 1 to 11.

The ring body 40 has two opposite curved inner portions 44 and 46 which are separated by recessed hinging apertures 48 and 50. These hinging apertures are defined by parallel guide surfaces 41, 43, 45, and 47, as best shown in FIG. 14, and denoted by numerals 40a and 40b.

The hinge pin openings communicate with the groove 42 in the ring 40 and thereby provide access spaces for installation of hinge pins 56 and 58, and when a suturing collar such as the collar 8 is installed, these hinge pin extremities are protectively covered. Mounted for hinging movement on the pins 56 and 58 are two valve flap elements 52 and 54, as shown in a closed position in FIG. 13, and also indicated in an open position in broken lines in FIG. 13. These valve flap elements are of a semilunar configuration and are formed with relatively thick hinging extremities and relatively thin abutting edges, as may be noted from an inspection of FIGS. 13 and 14. The location of the hinging pins 56 and 58 is arranged in the relatively thick hinging extremities along an axes of hinging 62 which lies below a center 60 passing through the relatively thin valve elements 52 and 54.

It will be apparent that when the valve elements assume the position shown in FIG. 12, they are prevented from further movement in one direction, and yet are always free to move upwardly into the dotted-line positions shown in FIG. 13.

The configuration of the relatively thick hinging portions of these flap elements are further formed of an arcuate shape such that surfaces of these hinging portions tend to move closely adjacent to the inner edges of the hinging apertures 48 and 50 which provides a useful function of constantly excluding a flow of fluid between these surfaces at all times, whether the valve elements are in an open or closed position. The parallel guide surfaces 41, 43, 45, and 47 also cooperate with flat sides of the hinging portions in the manner already described to constantly maintain the hinging movement of these valve elements in a carefully guided manner.

In FIGS. 15 to 21, another desirable form of valve hinging means is illustrated wherein a plurality of valve elements are supported in a retainer ring body by key means which limit arcs of rotation through which the valve elements may move in response to systolic and diastolic pressures. The key means include bearing pins formed with elongated keying portions which are constructed and arranged in key slots or key beds provided in outer valve extremities as described below.

Figure 15:
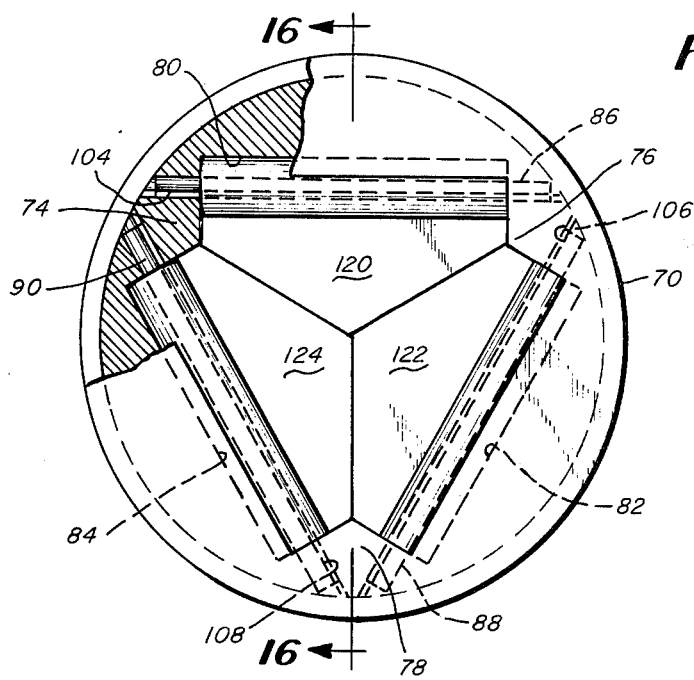
FIG. 15 is a plan view of another desirable form of heart valve flap and retaining ring assembly of the same general nature as the assemblies indicated in FIGS. 1 through 14, but further illustrating another hinging arrangement.

As indicated in FIG. 15, numeral 70 denotes a retainer ring body through which fluid may be conducted, and this ring body is generally similar in form and construction to the retainer rings earlier described. The ring body 70 at its outer periphery is formed with a grooved surface 72 against which a suturing collar may be secured in the manner earlier disclosed.

Inner parts of ring 70 are relieved to form bearing portions 74, 76 and 78. At points between these bearing portions the ring 70 is further recessed to provide semi-cylindrically shaped hinging apertures denoted by numerals 80, 82 and 84. The bearing portions 74, 76 and 78 function to support a set of three bearing pins 86, 88 and 90 which extend chordally of the ring body 70 and have their extremities fixed in the bearing portions.

Thus extremities of bearing pin 86 are mounted in fixed relation between parallel sides 92, 94 of bearing portions 74 and 76. Similarly extremities of bearing pin 88 are fixed between parallel sides 96 and 98 of bearing portions 76 and 78, and extremities of bearing pin 90 are fixed between parallel sides 100 and 102 of bearing portions 74 and 78.

Figure 19:
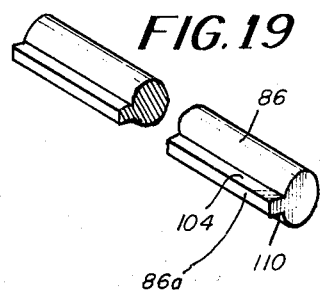
FIG. 19 is a detail perspective view of a bearing member having a key portion formed integrally therewith.

Each of the bearing pins is constructed with an elongated key portion, as is more clearly shown in FIG. 19, wherein the bearing pin 86 is indicated separately, and formed with a key portion 86a. These key portions are arranged to project inwardly toward the center of ring body 70, and are of generally rectangular cross section, as shown in FIG. 19, and present respective upper surfaces 104, 106, 108, and respective under-surfaces, of which the under-surface 110 is shown in FIG. 19, and is intended to be representative.

Figure 18:
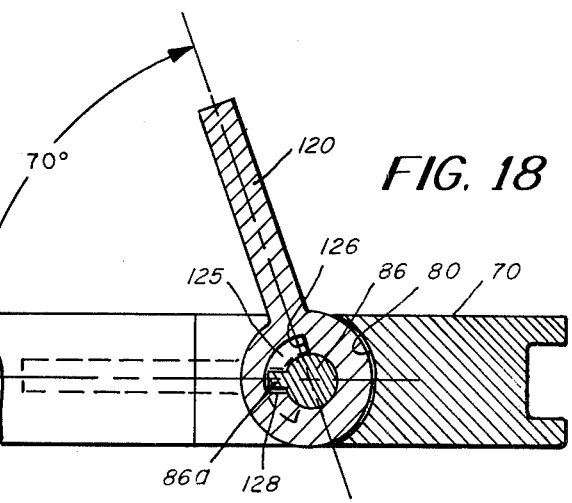
FIG. 18 is a fragmentary view partly in cross section illustrating a valve flap in a fully opened position.
Figure 21:
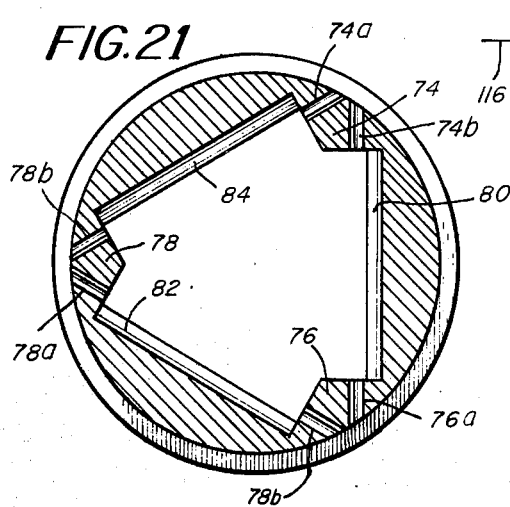
FIG. 21 is a plan cross sectional view of the retainer ring taken on the line 21—21 of FIG. 16 and illustrating sets of bearing slots and connecting keyways.

Extremities of the elongated key portions are received in and mate with complementary key slots formed in the bearing portions, as shown in FIG. 15, in a position such that upper and under surfaces of the key portions are spaced equidistantly from a horizontal plane passing centrally through the ring body 70, as suggested by the line 116 (FIG. 18). In FIG. 21, key slots 74a and 74b are indicated in bearing 74. Similarly, key slots 76a and 76b are shown in bearing 76, and key slots 78a and 78b have been shown in bearing portion 78.

Figure 16:
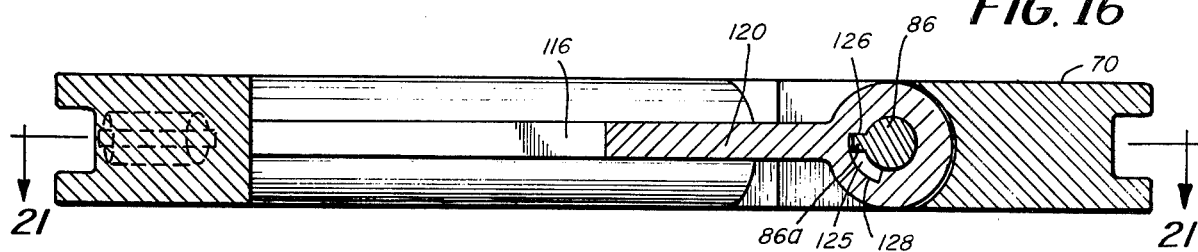
FIG. 16 is a cross section taken on the line 16—16 of FIG. 15.
Figure 17:
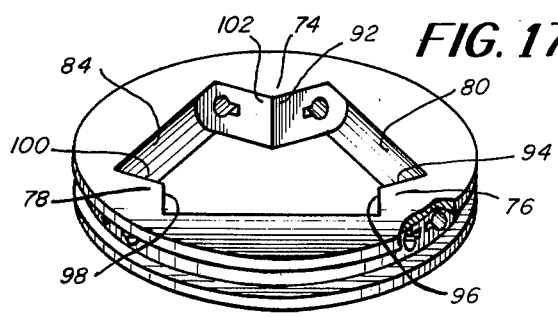
FIG. 17 is a perspective view of the retainer ring of FIG. 15 with valve flaps removed.
Figure 20:
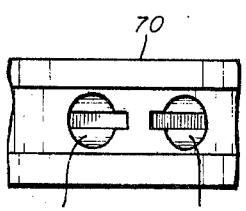
FIG. 20 is a fragmentary elevational view of a retainer ring part illustrating hinging pin openings formed therein.

Rotatably mounted on the bearing pins 86, 88 and 90 are valve flap elements 120, 122 and 124. Each of these valve flaps is formed with an outer cylindrical portion through which is drilled a hole for receiving respective bearing pins, as suggested in FIGS. 16 and 18. Along their inner sides, the bearing pin openings are enlarged, as best shown in FIGS. 16 and 20, to form arcuate slots or key beds. One of these arcuate key beds formed in valve flap 120 is indicated by numeral 125. It will be observed that the arcuate length of each of the key parts are defined by upper and lower end walls including an upper end wall 126 and a lower end wall 128 in valve flap 120.

The arrangement and location of the end walls in each cylindrical extremity of the valve flap is chosen such that movement of the valve flaps takes place through limited arcs of rotation which extend from the fully closed position of each valve flap shown in FIG. 1 to the fully opened position suggested by the valve flap 120 in FIG. 18. It will also be noted that the end wall 126 of valve flap 120 abuts against the surface 104 of bearing pin 86, which surface functions as a stop for precisely locating the valve flap 120 in a precisely closed position. Likewise, the end wall 128 abuts against the underside 110 of member 86, as shown in FIG. 18, to control the degree of opening of the valve flap 120 which may, for example, consist in an arc of travel of approximately 70°.

Since the key portions formed on the bearing pins extend throughout the length of the bearing and are engaged in key beds of similarly extended length, a very long life and accurate bearing assembly is realized of a nature which is particularly suitable for heart implant purposes.

It should also be noted that the cylindrical shape of the valve flap extremities, slidably contained against the cylindrical hinging apertures in the ring, provide a very desirable sealing action in excluding passage of a fluid such as blood between the valve extremities and the ring, and at the same time, the likelihood of clogging or jamming of any of these valve parts is clearly minimized.

We claim:

1. A prosthetic valve structure for use in cardiovascular surgery, said valve structure comprising a ring body having a fluid passageway formed centrally therethrough, the outer peripheral surface of the ring body being formed with a groove extending therearound, means in the groove for attaching the ring body within a fluid conduit of a patient's body, inner parts of the ring body being removed to form spaced apart bearing portions, each of said bearing portions presenting converging sides which extend radially inwardly in intersecting relationship, portions of the ring body lying between the said bearing portions being recessed to form concaved bearing apertures, bearing pin elements fixed in the bearing portions and extending chordally through the bearing apertures, a plurality of triangular valve flaps, said triangular valve flaps having cylindrical hinge sections rotatably mounted in the concaved bearing apertures on the respective pin elements and being movable in response to flow of blood to open and close the said flood passageway of the ring body, and elongated key means formed on each of the bearing pin elements in radially inwardly extending relationship for limiting the arcs of rotation through which the cylindrical hinge sections may be moved.

2. The invention of claim 1 in which the elongated key means present respective upper and lower flat sides which are spaced equidistantly above and below a plane passing centrally between upper and lower surfaces of the ring body.

3. The invention of claim 2 in which the cylindrical hinge sections are formed with arcuate key beds defined by end walls engageable with said upper and lower sides of the key means to limit open and closed position of the flaps.

4. The invention of claim 3 in which arcs of curvature of the concave bearing apertures coincide and mate with adjacent cylindrical sections to constitute seating surfaces which exclude passage of blood therebetween.

5. The invention of claim 4 in which extremities of the cylindrical sections are slideably engageable with respective adjacent bearing portions.

* * * * *